(12) United States Patent
Venkataraman et al.

(10) Patent No.: US 10,383,694 B1
(45) Date of Patent: Aug. 20, 2019

(54) MACHINE-LEARNING-BASED VISUAL-HAPTIC FEEDBACK SYSTEM FOR ROBOTIC SURGICAL PLATFORMS

(71) Applicant: Verb Surgical Inc., Mountain View, CA (US)

(72) Inventors: Jagadish Venkataraman, Menlo Park, CA (US); Denise Ann Miller, Scotts Valley, CA (US)

(73) Assignees: JOHNSON & JOHNSON INNOVATION—JJDC, INC., New Brunswick, NJ (US); VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/129,593

(22) Filed: Sep. 12, 2018

(51) Int. Cl.
*A61B 34/00* (2016.01)
*A61B 34/35* (2016.01)
(Continued)

(52) U.S. Cl.
CPC ............. *A61B 34/76* (2016.02); *A61B 34/25* (2016.02); *A61B 34/35* (2016.02); *A61B 34/74* (2016.02); *A61B 1/04* (2013.01); *A61B 34/20* (2016.02); *A61B 2034/305* (2016.02); *A61B 2034/743* (2016.02)

(58) Field of Classification Search
CPC .......... A61B 34/25; A61B 34/35; A61B 34/74
See application file for complete search history.

(56) References Cited

U.S. PATENT DOCUMENTS 9,218,565 B2 * 12/2015 Chatterjee ............... G06F 3/016
2007/0233267 A1 * 10/2007 Amirouche ........... A61F 2/4684
623/20.14
(Continued)

FOREIGN PATENT DOCUMENTS

WO   WO2018-125917 A1   7/2018

OTHER PUBLICATIONS

International Search Report and Written Opinion dated Jun. 11, 2019 for related PCT Application No. PCT/US2018/051567 28 Pages.
(Continued)

*Primary Examiner* — Edward Park
(74) *Attorney, Agent, or Firm* — Womble Bond Dickinson (US) LLP

(57) ABSTRACT

Embodiments described herein provide various examples of a visual-haptic feedback system for generating a haptic feedback signal based on captured endoscopy images. In one aspect, the process for generating the haptic feedback signal includes the steps of: receiving an endoscopic video captured for a surgical procedure performed on a robotic surgical system; detecting a surgical task in the endoscopic video involving a given type of surgical tool-tissue interaction; selecting a machine learning model constructed for analyzing the given type of surgical tool-tissue interaction; for a video image associated with the detected surgical task depicting the given type of surgical tool-tissue interaction, applying the selected machine learning model to the video image to predict a strength level of the depicted surgical tool-tissue interaction; and then providing the predicted strength level to a surgeon performing the surgical task as a haptic feedback signal for the given type of surgical tool-tissue interaction.

20 Claims, 7 Drawing Sheets

(51) Int. Cl.
    *A61B 1/04*         (2006.01)
    *A61B 34/20*      (2016.01)
    *A61B 34/30*      (2016.01)

(56) References Cited

U.S. PATENT DOCUMENTS

2014/0046128 A1   2/2014  Lee et al.
2019/0029757 A1*  1/2019  Roh ........................ A61B 34/10

OTHER PUBLICATIONS

Gessert, N. et al., "Force Estimation from OCT Volumes using 3D CNNs", International Journal of Computer Assisted Radiology and Surgery, Jul. 2018 (Published online: May 4, 2018), vol. 13, No. 7, pp. 1073-1082.

Goa, C. et al., "Learning to See Forces: Surgical Force Prediction with RGB-Point Cloud Temporal Convolutional Networks", Conference: MICCAI 2018 workshop: CARE(Computer Assisted and Robotic Endoscopy), Aug. 2018, internal pp. 1-10.

Wiles, A. I. et al., "Towards Retrieving Force Feedback in Robotic-Assisted Surgery: A Supervised Neuro-Recurrent Vision Approach.", IEEE Transactions on Haptics, Jul.-Sep. 2017, vol. 10, No. 3, pp. 431-443.

* cited by examiner

US 10,383,694 B1

MACHINE-LEARNING-BASED VISUAL-HAPTIC FEEDBACK SYSTEM FOR ROBOTIC SURGICAL PLATFORMS

TECHNICAL FIELD

The present disclosure generally relates to building surgical video analysis tools, and more specifically to systems, devices and techniques for generating a haptic feedback signal based on captured endoscopy images depicting a type of surgical tool-tissue interaction and providing the haptic feedback signal to a surgeon performing the surgical task involving the type of surgical tool-tissue interaction.

BACKGROUND

In a conventional surgical procedure, including a conventional laparoscopic procedure, a surgeon who holds one or two surgical tools and then applies the one or two surgical tools on a tissue, e.g., by pushing or pulling on the tissue, can actually feel the pressure or tension applied on the tissue as a result of a physical haptic feedback transmitted through the surgical tools back to the surgeon. Based on this physical haptic feedback, the surgeon can quickly adjust the applied force until a desirable physical haptic feedback is received.

In contrast, in a robotic surgery platform, surgeons working with remote controllers are physically and mechanically detached from the robotic arms and end effectors/surgical tools interacting with the surgical subject, and as such do not receive physical haptic feedback. To gauge the applied forces, a "visual haptic" technique is often used. More specifically, surgeons watch visual appearances of tissues under applied forces in video feeds on video monitors and use their experiences and expertise to make mental mappings between what they see on the video feeds and what they think the applied forces on the tissues should be, and make adjustments on the applied forces if necessary.

However, there can be a vast amount of inconsistency in judging the applied forces on the tissues based on the visual appearances from one surgeon to another surgeon and among surgeons of different skill/experience levels. It can be expected that a more experienced surgeon can make more accurate mappings based on the visual haptics than a less experienced surgeon. Unfortunately, there is no good way to provide a consistent correlation between what a surgeon sees in the video and what the applied force really is.

SUMMARY

In one aspect, a process for generating a haptic feedback based on a captured endoscopic video depicting an interaction between one or more surgical tools and a tissue during a robotic surgical procedure is disclosed. This process can begin by receiving an endoscopic video captured for a surgical procedure performed on a robotic surgical system. The process then detects a surgical task in the endoscopic video that involves a given type of surgical tool-tissue interaction caused by applying a force on a tissue using one or more surgical tools. Next, the process selects a machine learning model from a set of machine learning models based on the detected surgical task, wherein each machine learning model in the set of machine learning models is trained to analyze a given type of surgical tool-tissue interaction. For a video image associated with the detected surgical task depicting the given type of surgical tool-tissue interaction, the process then applies the selected machine learning model to the video image to predict a strength level of the depicted surgical tool-tissue interaction. Finally, the process provides the predicted strength level to a surgeon performing the surgical task as a haptic feedback signal for the given type of surgical tool-tissue interaction.

In some embodiments, the process detects the surgical task in the endoscopic video involving the given type of surgical tool-tissue interaction by detecting one or more surgical tools coming into view.

In some embodiments, the selected machine learning model is trained to classify a video image or a sequence of video images depicting the given type of surgical tool-tissue interaction as one of a set of predetermined strength levels defined for the given type of surgical tool-tissue interaction.

In some embodiments, the process applies the selected machine learning model to the video image to predict the strength level of the depicted surgical tool-tissue interaction by classifying the video image as one of the set of predetermined strength levels for the given type of surgical tool-tissue interaction based on analyzing a visual appearance of the depicted surgical tool-tissue interaction.

In some embodiments, the process provides the predicted strength level to the surgeon performing the surgical task by: converting the predicted strength level by the selected machine learning model into a physical feedback signal; and communicating the converted physical feedback signal to the surgeon performing the surgical task via a user interface device (UID) of the robotic surgical system.

In some embodiments, the physical feedback signal is a mechanical vibration, and the process communicates the converted physical feedback signal to the surgeon via the UID of the robotic surgical system by transmitting the mechanical vibration to a remote controller of the UID held by the surgeon so that the surgeon can directly feel the physical feedback signal.

In some embodiments, the process further includes using different frequencies or different intensities of the mechanical vibration to represent different predicted strength levels of the given type of surgical tool-tissue interaction.

In some embodiments, the physical feedback signal is an auditory signal, and the process communicates the converted physical feedback signal to the surgeon via the UID of the robotic surgical system by transmitting the auditory signal using a speaker of the UID so that the surgeon can directly hear the physical feedback signal.

In some embodiments, the process further includes using different volumes or different pitches of the auditory signal to represent different predicted strength levels of the given type of surgical tool-tissue interaction.

In some embodiments, the given type of surgical tool-tissue interaction is caused by applying a compression force on the tissue using the one or more surgical tools.

In some embodiments, the given type of surgical tool-tissue interaction is caused by applying a tensile force on the tissue using the one or more surgical tools.

In some embodiments, the given type of surgical tool-tissue interaction is caused by applying the force using a single surgical tool on the tissue.

In some embodiments, the given type of surgical tool-tissue interaction is caused by applying the force using two or more surgical tools on the tissue.

In some embodiments, the given type of surgical tool-tissue interaction is associated with one of: (1) tying a surgical knot during a suture operation; (2) pulling on the tissue during a cautery operation; and (3) compressing the tissue during a stapling operation.

In some embodiments, the set of predetermined strength levels includes a maximum strength level. If the predicted strength level is determined to be above the maximum strength level, the process further includes generating a warning signal to be communicated to the surgeon.

In some embodiments, prior to using the selected machine learning model, the process further includes training the selected machine learning model by: (1) receiving a set of endoscopic videos; (2) processing each of the endoscopic videos to extract from the endoscopic video one or more segments that depict the given type of tool-tissue interaction; (3) for each of the extracted video segments, annotating video images depicting the given type of tool-tissue interaction according to a set of predetermined strength levels; and (4) using the annotated video images as ground truth information to train a machine learning model to analyze the given type of surgical tool-tissue interaction.

In another aspect, a system for generating a haptic feedback based on a captured endoscopic video depicting an interaction between one or more surgical tools and a tissue during a robotic surgical procedure is disclosed. This system includes: one or more processors; a memory coupled to the one or more processors; a receiving module for receiving an endoscopic video captured for a surgical procedure performed on a robotic surgical system; a detection module for detecting a surgical task in the endoscopic video that involves a given type of surgical tool-tissue interaction caused by applying a force on a tissue using one or more surgical tools; a selection module for selecting a machine learning model from a set of machine learning models based on the detected surgical task, wherein each machine learning model in the set of machine learning models is trained to analyze a given type of surgical tool-tissue interaction; a machine learning module configured to, for a video image associated with the detected surgical task depicting the given type of surgical tool-tissue interaction, apply the selected machine learning model to the video image to predict a strength level of the depicted surgical tool-tissue interaction; and a user interface module for providing the predicted strength level to a surgeon performing the surgical task as a haptic feedback signal for the given type of surgical tool-tissue interaction.

In some embodiments, the system further includes a machine-learning-model training module for training the selected machine learning model with the steps of: (1) receiving a set of endoscopic videos; (2) processing each of the endoscopic videos to extract from the endoscopic video one or more segments that depict the given type of tool-tissue interaction; (3) for each of the extracted video segments, annotating video images depicting the given type of tool-tissue interaction according to a set of predetermined strength levels; and (4) using the annotated video images as ground truth information to train a machine learning model to analyze the given type of surgical tool-tissue interaction.

In yet another aspect, a robotic surgical system is disclosed. This robotic surgical system includes: one or more surgical tools each coupled to a robotic arm; an endoscope configured to capture endoscopic videos; a receiving module for receiving a captured endoscopic video for a surgical procedure performed on the robotic surgical system; a detection module for detecting a surgical task in the endoscopic video that involves a given type of surgical tool-tissue interaction caused by applying a force on a tissue using the one or more surgical tools; a selection module for selecting a machine learning model from a set of machine learning models based on the detected surgical task, wherein each machine learning model in the set of machine learning models is trained to analyze a given type of surgical tool-tissue interaction; a machine learning module configured to, for a video image associated with the detected surgical task depicting the given type of surgical tool-tissue interaction, apply the selected machine learning model to the video image to predict a strength level of the depicted surgical tool-tissue interaction; and a user interface module for providing the predicted strength level to a surgeon performing the surgical task as a haptic feedback signal for the given type of surgical tool-tissue interaction.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1A:
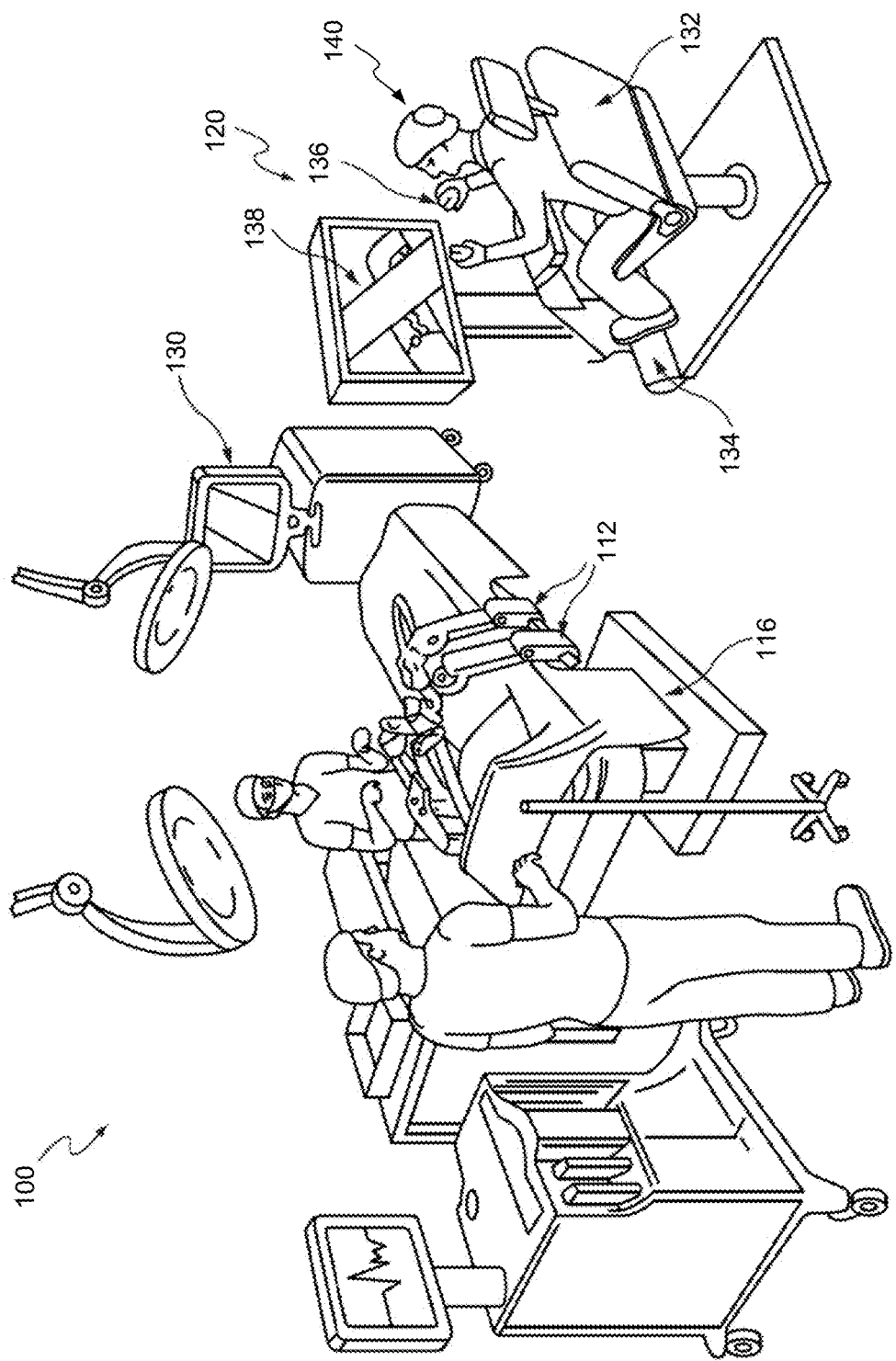
FIG. 1A shows a diagram illustrating an example operating room environment with a robotic surgical system in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout this patent disclosure, the term "strength level" is generally used to mean an intensity of a force applied by one or more surgical tools, directly or indirectly on a tissue of a body during a surgical procedure, wherein the applied force can include a compression force (e.g., by compressing a tissue) or a tension force (e.g., by pulling on the tissue). Moreover, the term "surgical tool-tissue interaction" is generally used to mean any interaction between one or more surgical tools and a tissue of a body that involves directly or indirectly applying a force (e.g., a compression force or a tension force) on the tissue by the one or more surgical tools. Generally, it is assumed that this surgical tool-tissue interaction would result in a certain degree of change in shape of the tissue, such as a length, a thickness, a curvature, or an overall size of the tissue. Throughout this patent disclosure, a given type of surgical tool-tissue interaction is also referred to as a given type of "surgical task."

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures that involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exists and continues to be created as a result of a large number of surgical cases performed by many different surgeons from different hospitals. The simple fact of the existence of a huge (and constantly increasing) number of surgical videos of a particular surgical procedure makes processing and analyzing the surgical videos of the given procedure a potential machine learning problem.

As mentioned above, robotic surgical platforms generally lack a direct physical haptic feedback from surgical tools mounted on the robotic arms to the surgeons manipulating the surgical tools through remote controllers. As such, the surgeons operating the surgical tools attached to the robotic arms have to gauge the applied forces of the surgical tools on the organs or tissues, such as how tightly a surgical knot is being tied on a tissue or how tightly a tissue is being pulled by a grasper for cautery, based on visual feedback from endoscopic video feeds, e.g., by viewing a user display. In other words, the surgeons directly observe the video images of interactions between the surgical tools and the tissues in the endoscopic video feeds and gauge the applied forces based on mental interpretations of these visual images. Hence, this visual haptic technique relies heavily on the surgeon's experience to correlate a visual appearance of the surgical tool-tissue interaction to the physical strength of the interaction, and as a result can suffer from both inaccuracies and inconsistencies.

One of the objectives of this patent disclosure is to establish a correlation between a visual appearance of the surgical tool-tissue interaction in an endoscopic video feed and what the surgeon can physically "feel" via one or more user interface devices (UIDs) of the robotic surgical system through some form of physical feedback. To achieve this objective, various embodiments of this patent disclosure incorporate the experience-based visual haptic technique used on robotic surgical platforms into a machine-learning-based visual-haptic feedback system including various machine learning models. Each of these machine learning models, when properly trained (i.e., to teach the machine with training data), can establish accurate and consistent correlations between video images depicting various degrees of surgical tool-tissue interactions and the actual amount of force applied by the surgical tools on the tissues. Hence, the proposed machine learning models can also be referred to as "visual-haptic machine learning models" or "visual-haptic models." More specifically, each unique visual-haptic model can be constructed for a particular type of surgical tool-tissue interaction that involves directly or indirectly applying a compression or a tension force on a tissue by one or more surgical tools. For example, one such visual haptic machine learning model can be constructed for predicting the tightness levels of a surgical knot in a suturing operation (wherein two forceps indirectly apply a force on a tissue through a surgical knot being tied), another such machine learning model can be constructed for predicting the tension levels on a tissue when pulling the tissue with a grasper in preparation for cautery, and yet another such visual-haptic model can be constructed for predicting the compression levels on a tissue when squeezing the tissue with a stapler in preparation for stapling.

In various embodiments, the disclosed machine-learning-based visual-haptic feedback system also includes a visual-haptic analysis module that includes trained visual-haptic models. Using a trained visual-haptic model of a given type of surgical tool-tissue interaction, the disclosed visual-haptic analysis module can automatically segment an endoscopic video to detect video images containing the given type of surgical tool-tissue interaction and to predict in real time the strength levels of the surgical tool-tissue interaction depicted in these video images, e.g., to predict how tight or loose a surgical knot is or how tightly or loosely a tissue is held by one or more surgical tools.

In various embodiments, the disclosed visual-haptic feedback system also includes a haptic feedback signal generator coupled between the disclosed visual-haptic analysis module and UIDs of a robotic surgical system. In various embodiments, the image classification outputs from a given visual-haptic model can be fed to the feedback signal generator to be converted to appropriate physical feedback signals, also referred to as "haptic cues." These haptic cues are subsequently communicated to the surgeons/users of the robotic surgical system through the UIDs as physical feedback to indicate the current strength levels of the surgical tool-tissue interaction, such as the tightness of the surgical knot or the tissue grab. Based on the received physical feedback, a surgeon can quickly adjust the force on the surgical tools to effectuate a desirable strength level on the tissue being manipulated.

In some embodiments, to establish a machine learning model for a given type of surgical tool-tissue interaction, a large number of video frames, e.g., thousands to hundreds of thousands of those containing the images depicting the given type of surgical tool-tissue interaction can be collected from relevant surgical videos. Next, the images are annotated/labeled into a set of predetermined strength levels by a group of experts who are trained to assign proper strength levels to video images of the surgical tool-tissue interactions based on a set of established standards for mapping visual appearances of surgical tool-tissue interactions to the set of predetermined strength levels. The annotated video images of a given type of surgical tool-tissue interaction can then be used as ground truth/training data to train a corresponding visual-haptic model in the surgical tool-tissue interaction. Once the visual-haptic model has been trained with the training data, the visual-haptic model can be incorporated into the disclosed visual-haptic analysis module that is configured to receive real-time endoscopic videos.

Consequently, the disclosed visual-haptic feedback system allows for establishing a correlation between a visual appearance of the surgical tool-tissue interaction in a surgical video feed of a robotic surgical procedure and what the surgeon performing the surgical procedure can physically feel via one or more UIDs of a robotic surgical system. Integrating the disclosed visual-haptic feedback system with a robotic surgical system can make the interpretation of the visual images of a given type of surgical tool-tissue interaction an automatic and highly standardized operation, thereby removing the need of requiring the surgeon to mentally interpret the visual images and the uncertainty and inconsistency that are associated with such interpretations. While the disclosed visual-haptic feedback system and technique are generally described with the help of a few specific operations associated with surgical procedures, such as suturing, cautery, and stapling, the present disclosure is not meant to be limited to the above-specified operations. In general, the disclosed visual-haptic feedback system and technique are applicable to any surgical procedure that involves an interaction between one or more surgical tools and a tissue of the body, for which the surgery procedure can be captured in a video feed. Note that the disclosed visual-haptic feedback systems can also make the robotic surgical experiences significantly more realistic and natural for the surgeons.

FIG. 1A shows a diagram illustrating an example operating room environment with a robotic surgical system 100 in accordance with some embodiments described herein. As shown in FIG. 1A, robotic surgical system 100 comprises a surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., tele-operation). User console 120 may be located in the same operation room as robotic surgical system 100, as shown in FIG. 1A. In other environments, user console 120 may be located in an adjacent or nearby room, or tele-operated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically-driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 134 and/or UIDs 136 to manipulate various surgical tools/end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures, including but not limited to, robotic surgical system 100 cleaning and/or sterilization, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 1B:
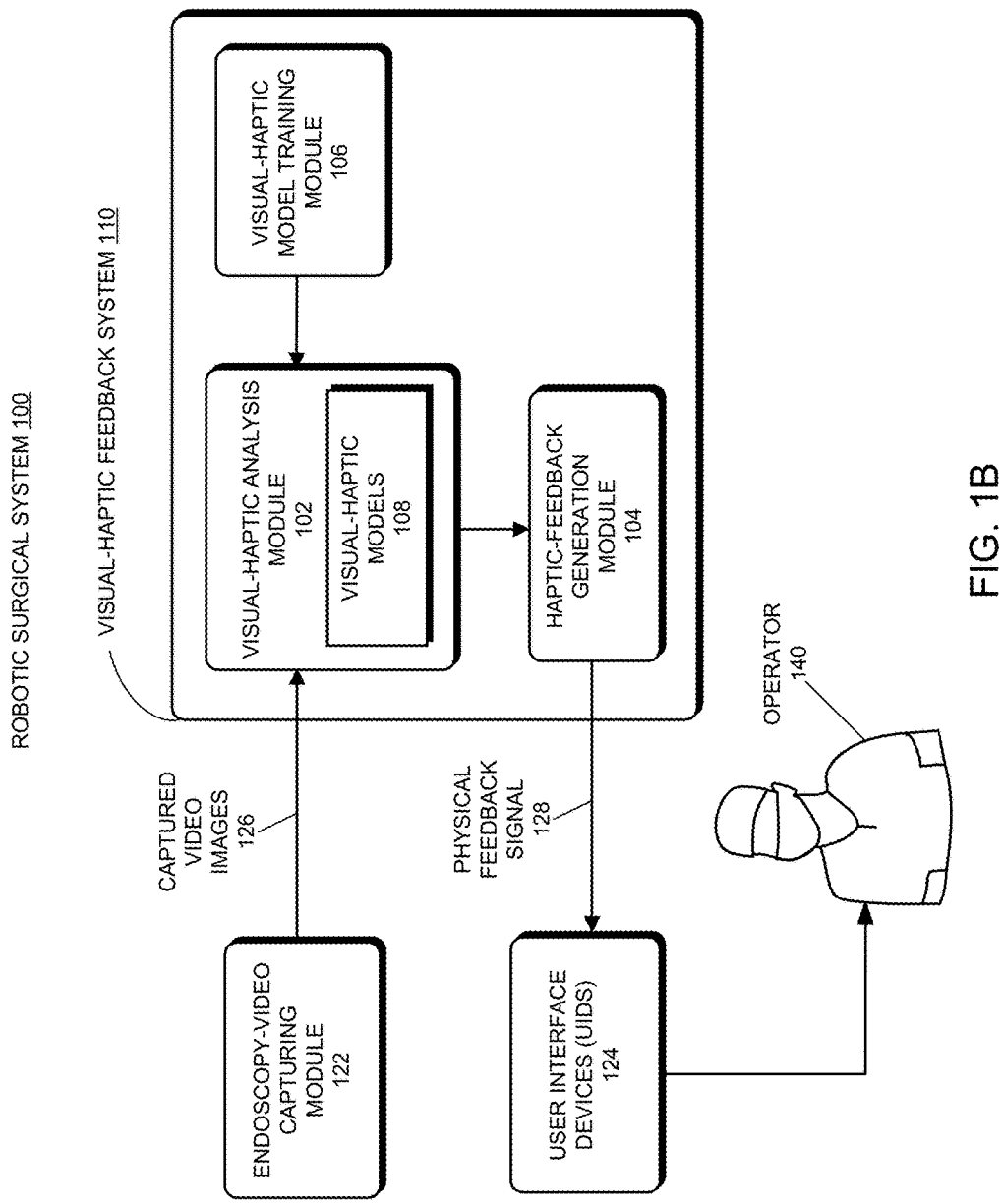
FIG. 1B shows a block diagram of an exemplary visual-haptic feedback system implemented in the robotic surgical system in FIG. 1A in accordance with some embodiments described herein.

FIG. 1B shows a block diagram of an exemplary visual-haptic feedback system 110 implemented in robotic surgical system 100 in FIG. 1A in accordance with some embodiments described herein. As can be seen in FIG. 1B, visual-haptic feedback system 110 includes a visual-haptic analysis module 102, a haptic-feedback-generation module 104, and a visual-haptic model training module 106, which are coupled in the illustrated order. Visual-haptic feedback system 110 can be implemented as a module within control tower 130 (not shown) of robotic surgical system 100 as a part of robotic surgical system 100. In the embodiment of FIG. 1B, robotic surgical system 100 also includes an endoscopy-video capturing module 122 (not explicitly shown in the embodiment of system 100 depicted in FIG. 1A) and one or more user interface devices (UIDs) 124. UIDs 124 can include handheld UIDs 136 described in conjunction with FIG. 1A. However, UIDs 124 can include other types of user interface devices for conveying physical feedback signals to the user of robotic surgical system 100, such as a speaker or a monitor.

For clarify and simplicity purposes, various modules of robotic surgical system 100 depicted in FIG. 1A, such as some components of surgeon console 120, control tower 130, surgical robotic arms 112, and robotic surgical platform 116 are not explicitly shown in FIG. 1B. However, these modules are also integral parts of the embodiment of robotic surgical system 100 depicted in FIG. 1B. For example, the disclosed visual-haptic feedback system 110 can be implemented as a module within control tower 130 in form of computer software, electronic hardware, or combinations of both.

As shown in FIG. 1B, visual-haptic analysis module 102 of the disclosed visual-haptic feedback system 110 is coupled to endoscopy-video capturing module 122 of robotic surgical system 100. In some embodiments, endoscopy-video capturing module 122 is configured to capture and record endoscopic videos and/or still images during a live robotically assisted surgical procedure. Visual-haptic analysis module 102 is configured to receive the captured videos and/or still images (collectively referred to as "captured video images 126" hereinafter) from endoscopy-video capturing module 122 and perform real-time video and image processing to analyze haptic information in the captured videos and still images.

More specifically, visual-haptic analysis module 102 includes a set of visual-haptic models 108, wherein each of the set of visual-haptic models 108 is used to process videos and images containing a particular type of surgical tool-tissue interaction. For example, one visual-haptic model 108 can be used to analyze and determine tightness levels for surgical knots depicted in captured video images 126. Another visual-haptic model 108 can be used to analyze and determine the tension levels of a tissue pulled by a grasper in preparation for cautery depicted in captured video images 126. Yet another visual-haptic model 108 can be used to analyze and determine the compression levels of a stapler applied on a tissue prior to firing the stapler depicted in captured video images 126. These are just some examples for the possible use of visual-haptic models 108. It can be understood that, over time, visual-haptic models 108 can include an increasingly large number of models trained to process even more types of surgical tool-tissue interactions occurring in various robotically assisted surgical procedures. In various embodiments, visual-haptic analysis module 102 is also configured to determine the type of surgical tool-tissue interaction depicted in a segment of the captured video or a still image and subsequently selects a corresponding model from the set of visual-haptic models 108 to process the segment of video or the still image. In various embodiments, a given visual-haptic model 108 can include a regression model, a deep neural network-based model such as a convolutional neural network (CNN) or a recurrent neural network (RNN), a support vector machine, a decision tree, a Naive Bayes classifier, a Bayesian network, or a k-nearest neighbors (KNN) model.

In some embodiments, a selected visual-haptic model 108 in visual-haptic analysis module 102 is configured to automatically analyze video images 126 of a captured endoscopic video containing a corresponding type of surgical tool-tissue interaction. More specifically, for each video image/frame in the endoscopic video containing the given type of interaction in the endoscopic video containing the given type of interaction, the selected visual-haptic model 108 can make a prediction for and/or classifying the given video image/frame as one of a set of predetermined strength levels of the interaction. The outputs from visual-haptic analysis module 102 can include a sequence of computer-determined strength levels corresponding to a sequence of processed video images/frames. Note that if visual-haptic analysis module 102 operates in real time during a robotic surgical procedure, the output from visual-haptic analysis module 102 provides a real-time evaluation for the force applied on the tissue by the surgical tools.

Alternatively or additionally, for a sequence of video images/frames in the endoscopic video containing the given type of interaction, the selected visual-haptic model 108 can make a prediction for and/or classifying the sequence of video images/frames as one of a set of predetermined strength levels of the interaction. Note that processing multiple consecutive video images/frames to generate a corresponding strength level prediction can be more accurate than processing each video image/frame independently and generating a strength level prediction for each video image/frame. This is because a consecutive sequence of video images/frames can represent a continuous action to achieve a predetermined strength level and by processing the sequence of video frames collectively allows for identifying correlations among the sequence of video images/frames to facilitate generating a more accurate prediction for the sequence of video images/frames. In some cases, a surgeon may pause the action for a short period of time to allow the visual-haptic feedback system 110 more time to process the video images/frames. In such cases, processing a sequence of video images/frames collectively allows for recognizing the pause and predicting a single strength level for the sequence of video images/frames associated with the duration of the pause. Hence, the outputs from visual-haptic analysis module 102 can include multiple computer-determined strength levels corresponding to multiple sequences of processed video images/frames.

As illustrated in FIG. 1B, the output from visual-haptic analysis module 102 is received by haptic-feedback generation module 104. In some embodiments, haptic-feedback generation module 104 is configured to convert the strength levels predicted and output by visual-haptic analysis module 102 into a physical feedback signal 128 that can be transmitted to UIDs 124. Next, this physical feedback signal 128 can be communicated to an operator 140 (e.g., a surgeon 140 or a surgeon's assistant 140) performing or assisting the surgical procedure through UIDs 124 of robotic surgical system 100 to get the attention of operator 140.

Note that physical feedback signal 128 can be in one of a number of forms that can be quickly understood by operator 140. For example, physical feedback signal 128 can be an auditory feedback signal that can be heard by operator 140. In this case, physical feedback signal 128 can be configured with different tones, volumes, or pitches of the audio sound to represent different strength levels to operator 140, and the audio signal can be communicated to operator 140 through a speaker of UIDs 124. Physical feedback signal 128 can also be a mechanical signal such as a vibration that can be directly felt by the surgeon. In this case, physical feedback signal 128 can be configured with different amplitudes, frequencies, or numbers of discrete pulses of the vibration to represent different strength levels, and the mechanical signal can be communicated to operator 140 through one or both handheld controllers of UIDs 124. As another example, physical feedback signal 128 can be a visual signal that can be displayed on a monitor of UIDs 124 for operator 140 to view. In some embodiments, a portion of or the entire haptic-feedback generation module 104 can be integrated with UIDs 124 of robotic surgical system 100 to perform the aforementioned functions.

Note that the output from haptic-feedback generation module 104 can be transmitted to operator 140 of robotic surgical system 100 in real time as a haptic feedback signal so that operator 140 can use this information to adjust the applied pressure or tension on the tissue in real time if the haptic feedback signal indicates that the applied pressure or tension is either above or below a desirable strength level.

As mentioned above, if physical feedback signal 128 is configured as a mechanical signal, the feedback signal can be transmitted to the remote controller(s) held by operator 140 so that the feedback signal can be directly felt by the hand(s) of operator 140.

Note that the proposed visual-haptic feedback system 110 provides a surgeon manipulating a tissue using one or more surgical tools in a robotic surgical system with real-time feedback of the applied force on the tissue, even when the surgeon does not receive a direct physical haptic feedback through the surgical tools. Furthermore, with the proposed visual-haptic feedback system, the surgeon does not have to rely on the "visual haptics," i.e., the mental interpretation of the applied force based on the visual appearance of the surgical tool-tissue interaction depicted in the video images. However, the surgeons can still use the conventional visual haptics to interpret and cross-reference the physical feedback signal 128 generated by visual-haptic feedback system 110.

Continuing referring to FIG. 1B, note that visual-haptic feedback system 110 also includes a visual-haptic model training module 106, which is configured to construct a new visual-haptic model 108 with training data, which is then added to visual-haptic models 108 in visual-haptic analysis module 102, and in some embodiments, to refine an existing visual-haptic model 108 with additional training data. As described above, a given visual-haptic model 108 is constructed to predict the strength levels of a particular type of surgical tool-tissue interaction, e.g., the tightness levels of a surgical knot, the tightness levels for a tissue grab in preparation for cautery, or the compression levels of a stapler applied on a tissue prior to firing the stapler. Consequently, each of these distinctive visual-haptic models 108 is constructed/trained in a separate model training process. More specifically, prior to using a particular visual-haptic model 108 to analyze a particular type of surgical tool-tissue interaction depicted in a surgical video, the proposed system and technique also includes training such a visual-haptic model with training data comprised of annotated images of the same type of surgical tool-tissue interaction.

Figure 2:
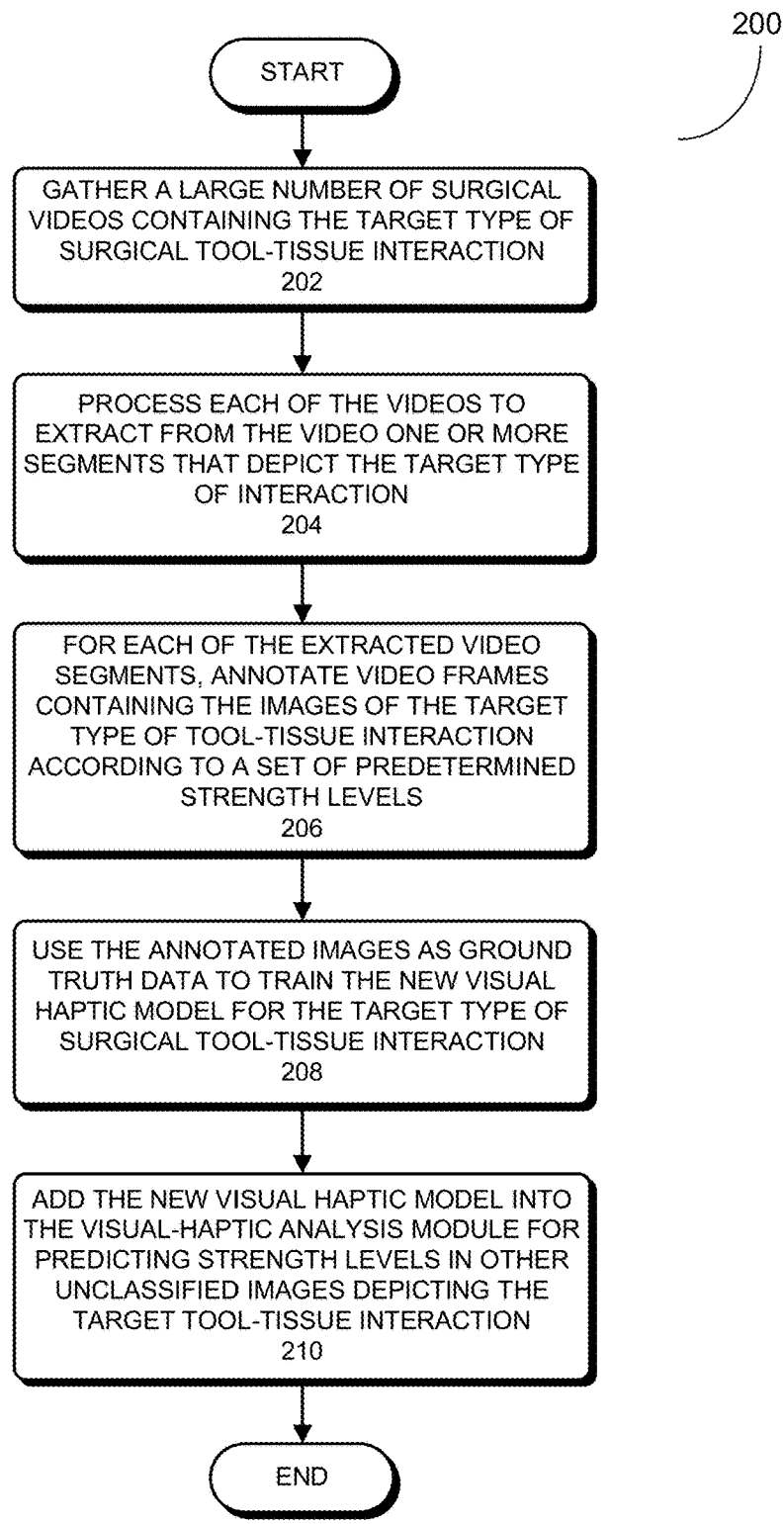
FIG. 2 presents a flowchart illustrating an exemplary process for constructing a new visual-haptic model for analyzing a particular type of surgical tool-tissue interaction in accordance with some embodiments described herein.

FIG. 2 presents a flowchart illustrating an exemplary process 200 for constructing a new visual-haptic model 108 for analyzing a particular type of surgical tool-tissue interaction in accordance with some embodiments described herein. In one or more embodiments, one or more of the steps in FIG. 2 may be omitted, repeated, and/or performed in a different order. Accordingly, the specific arrangement of steps shown in FIG. 2 should not be construed as limiting the scope of the technique.

Process 200 begins by gathering a large number of training videos containing the target type of surgical tool-tissue interaction, such as a suturing operation including tying surgical knots or pulling on a tissue in preparation for cautery (step 202). Note that the gathered training videos can include actual surgical procedure videos performed by surgeons for both robotic-assisted surgical procedures and non-robotic-assisted surgical procedures. Furthermore, the gathered training videos can include artificially generated procedure videos that are created for various training purposes. Moreover, the gathered training videos can include artificially generated procedure videos that are created specifically to provide training data for establishing the new visual-haptic model 108.

Process 200 next processes each of the videos to extract from the video one or more segments that depict the target type of tool-tissue interaction (step 204). Ideally, each selected video segment depicts a complete procedure of the target interaction from the initial contact of the one or more surgical tools with the tissue until a desired amount of applied force has been reached for the interaction between the one or more surgical tools and the tissue. For example, for tying a surgical knot, a desired amount of force can be considered to be reached when the two forceps tools pulling on the surgical knot have let go of the knot. As another example, for a cautery action, a desired amount of force is considered to be reached when a cautery tool begins to cauterize the tissue being pulled by a grasper. In yet another example, for stapling action, a desired amount of force is considered to be reached when the stapler compressing the tissue is fired. Note that from a single surgical video, multiple video segments of the same type of surgical tool-tissue interaction can be extracted.

Next, for each of the extracted video segments, process 200 then annotates video frames containing the images of the target type of tool-tissue interaction according to a set of predetermined strength levels (step 206). More specifically, for each video image depicting the target type of surgical tool-tissue interaction, the visual appearance of the surgical tool-tissue interaction, such as a suturing knot being tied or a tissue under tension or compression, is observed by an annotator or multiple annotators and then labeled/annotated with one of the set of predetermined strength levels by the one or multiple annotators.

In various embodiments, the set of predetermined strength levels can include a "proper," "moderate," or "intermediate" strength level that indicates that the amount of applied pressure or tension on the tissue is sufficiently high. In the case of tying suturing knots, when such an intermediate strength level is reached, the interaction between the one or more surgical tools and the tissue is complete. In the case of cautery or stapling, when such an intermediate strength level is reached, the subsequent action would typically take place (i.e., the cautery tool or the stapler begins to fire). Moreover, the set of predetermined strength levels can also include at least one strength level below the moderate strength level, which can be referred to as a "low strength" level, and at least one strength level above the moderate strength level, which can be referred to as a "high strength" level. For example, for tying the suturing knot, there can be three predetermined strength levels designated as loose (i.e., low), moderate, and tight (i.e., high). For the example of tissue-pulling in preparation for cautery, there can also be three predetermined strength levels designated as loose (i.e., low), moderate, and tight (i.e., high).

In some embodiments, the set of predetermined strength levels can also include two or more strength levels below the moderate strength level, and two or more strength levels above the moderate strength level. For example, for the suturing knot example, there can be five predetermined strength levels designated as too loose (i.e., too low), loose (i.e., low), moderate, tight (i.e., high), and too tight (i.e., too high). Note that using more levels in the set of predetermined strength levels allows for more accurately annotating an image depicting the target type of surgical tool-tissue interaction to a corresponding strength level, but on the other hand, would also make the annotation step 206 significantly more time-consuming. In some embodiments, the set of predetermined strength levels can include a maximum-safe strength level representing a safety threshold for the tissue under the applied force, and at least one more strength level above the maximum-safe strength level. For example, in the above example, the "tight" strength level can be designated as the maximum-safe strength level.

In some embodiments, step 206 is performed by annotators including clinical experts whose primary job is to review surgical videos, analyze images of different types of surgical tool-tissue interactions, and assign proper strength levels to the images depicting the various types of surgical tool-tissue interactions. As such, these experts are professionally trained to understand the correct mapping between visual appearances of the various surgical tool-tissue interactions (e.g., the shapes of surgical knots or the shapes of tissues under compression or tension) and applied forces of the surgical tools.

In some embodiments, prior to performing the image annotations of step 206, the set of predetermined strength levels are first established based on multiple expert opinions/guidelines. More specifically, a set of visual-appearance standards is first established by clinical experts and surgeons who have extensive experience in the related surgical procedures, such that each of the set of visual-appearance standards correlates a given predetermined strength level in the set of predetermined strength levels to a certain visual appearance of the surgical tool-tissue interaction. When multiple expert opinions/guidelines are gathered, a visual-appearance standard for a given strength level can be established as an average of the multiple expert opinions/guidelines. In the example of tissue-pulling in preparation for cautery, the expert opinions/guidelines can include mapping a given strength level of the tissue-pulling to a certain curvature along the edge of the tissue under tension. Clearly, a smaller curvature (i.e., the tissue being taut) would indicate a higher strength level of the pulling force and a larger curvature (i.e., the tissue being floppy) would indicate a lower strength level of the pulling force. Note that establishing a visual-appearance standard by gathering multiple expert opinions and taking the average of these values can significantly improve the reliability of the established standard.

Next, the set of established visual-appearance standards can be used as the nominal values (in the visual sense) for the set of predetermined strength levels. Hence, annotating the video images depicting the target type of surgical tool-tissue interaction involves assigning a predetermined strength level to a given image having the closest resemblance to the visual-appearance standard established for that predetermined strength level. In this manner, the annotated image data can accurately reflect the set of visual-appearance standards and as such be used as ground truth data.

After a sufficient amount of video images related to the target type of surgical tool-tissue interaction has been collected and properly annotated/labeled, process 200 includes using the annotated images as ground truth data to train the new visual-haptic model 108 for the target type of surgical tool-tissue interaction (step 208). As mentioned above, the new visual-haptic model 108 can be constructed as a regression model, a deep neural network-based model such as a convolutional neural network (CNN) or a recurrent neural network (RNN), a support vector machine, a decision tree, a Naive Bayes classifier, a Bayesian network, or a k-nearest neighbors (KNN) model. In some embodiments, training the new visual-haptic model 108 with the annotated training images involves using an imageNet-based deep learning framework such as VGGNet, ResNet, DenseNet, Dual Pathway Network, MobileNet or Inception v1-v3. However, other types of deep learning framework can be used to train the new visual-haptic model 108 with the annotated training images. Finally, process 200 adds the new visual-haptic model 108 into visual-haptic analysis module 102 for predicting the strength levels in other unclassified images depicting the target surgical tool-tissue interaction (step 210).

Figure 3:
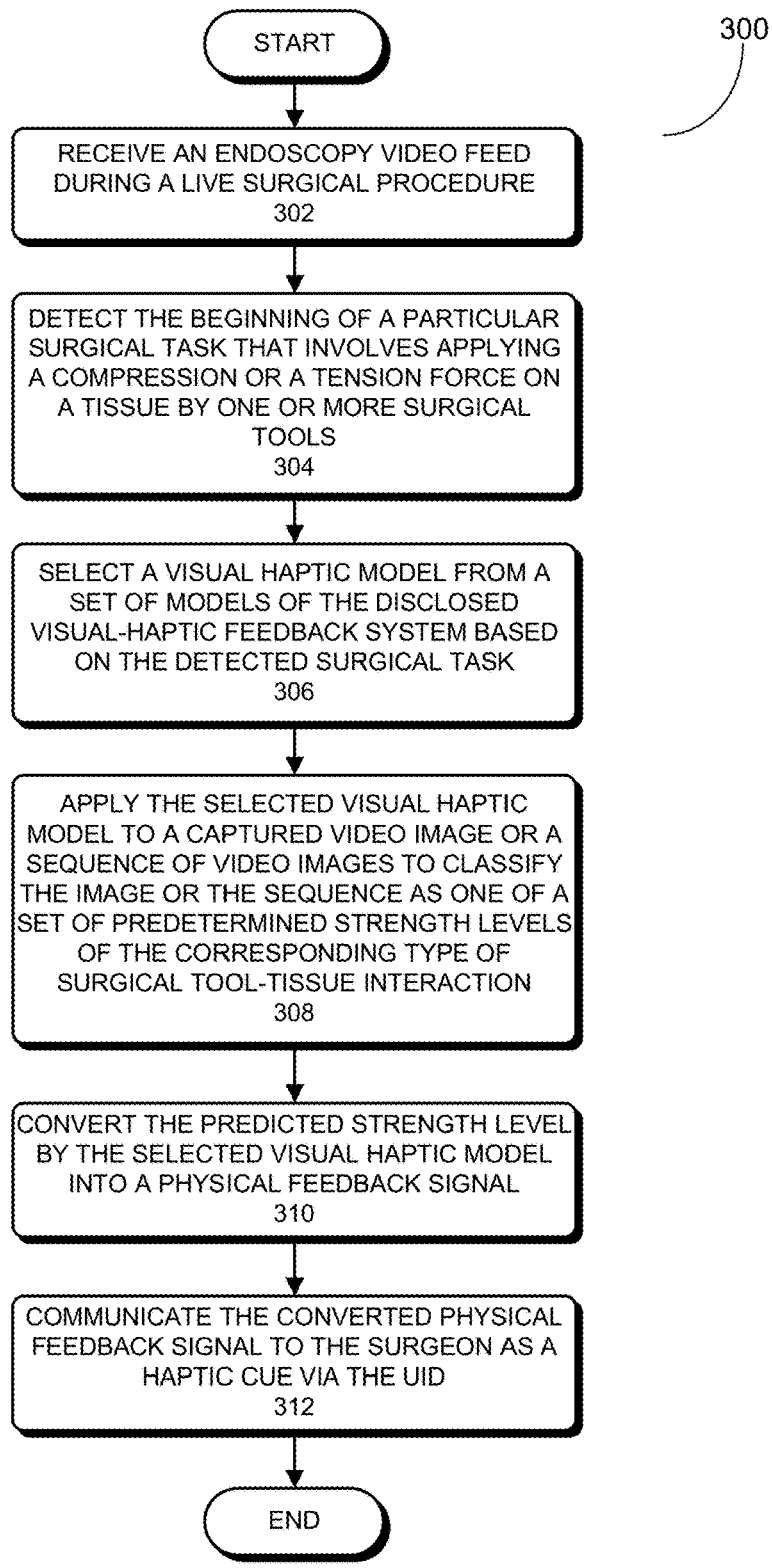
FIG. 3 presents a flowchart illustrating an exemplary process for providing a surgeon operating in a robotic surgical system with real-time haptic feedback using the disclosed visual-haptic feedback system in accordance with some embodiments described herein.

FIG. 3 presents a flowchart illustrating an exemplary process 300 for providing a surgeon operating in a robotic surgical system with real-time haptic feedback using the disclosed visual-haptic feedback system in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique. Note that process 300 of FIG. 3 can be understood in conjunction with visual-haptic feedback system 110 described in FIG. 1B.

Process 300 begins by receiving an endoscopic video feed during a live surgical procedure performed on a robotic surgical system (step 302). Next, process 300 detects the beginning of a particular surgical task (i.e., a given type of surgical tool-tissue interaction) that involves applying a compression force or a tension force on a tissue using one or more surgical tools (step 304). In some embodiments, process 300 can detect such an event by first detecting a particular surgical tool involved in such an event coming into view. For example, for a suturing task, this step may involve detecting two pairs of forceps coming into view. For a stapling task, this step may involve detecting a stapler coming into view. As another example, for a cautery task, this step may involve detecting a pair of tissue-grasping forceps coming into view. In some embodiments, process 300 can also detect the beginning of the surgical task based on an automatic segmentation of the received endoscopic video. For example, process 300 can be integrated with an endoscopic video segmentation tool, which is configured to automatically identify the beginnings of a set of predefined surgical phases and one or more predefined surgical tasks within each of the set of predefined surgical phases. In these embodiments, process 300 can begin processing the video frames to extract visual haptic information when the segmentation tool identifies a surgical task involving applying a compression force or a tension force on a tissue using one or more surgical tools.

Next, process 300 selects a visual-haptic model from a set of visual-haptic models of the disclosed visual-haptic feedback system based on the detected surgical task (step 306). For example, if the detected surgical task is a suturing operation, process 300 selects a visual-haptic model constructed to process video images depicting tying a surgical knot on a tissue with two forceps tools. If the detected surgical task is a cautery operation, process 300 selects a visual-haptic model constructed to process video images depicting pulling a tissue with a pair of tissue-grasping forceps in preparation for cautery. Alternatively, if the detected surgical task is a stapling operation, process 300 selects a visual-haptic model constructed to process video images depicting clamping down on a tissue by a stapler in preparation for stapling.

Next, for a captured video image or a sequence of video images associated with the detected surgical task, process 300 applies the selected visual-haptic model to the video image or the sequence of video images to classify the image or the sequence of video images as one of a set of predetermined strength levels of the corresponding type of surgical tool-tissue interaction (step 308). For example, if the detected surgical task is a suturing operation and the corresponding visual-haptic model includes three predetermined tension levels: tight, moderate, and loose, processing the captured video image in step 308 by the selected visual-haptic model will generate an output as being one of these three tension levels. In some embodiments, the set of predetermined strength levels can include a maximum-safe strength level representing a safety threshold for the tissue under the applied force, and at least one more strength level above the maximum-safe strength level. As described above, the output from the selected visual-haptic model is a "visual haptic" signal because the model analyzes the video image or the sequence of video images and outputs a prediction of the tool-tissue-interaction strength depicted in the video image or the sequence of video images. Note that using the proposed visual-haptic model, the prediction of the tool-tissue-interaction strength becomes an automatic process, and the accuracy of the prediction is determined by the quality of the selected visual-haptic model.

After extracting the strength level information for the video image or the sequence of video images, process 300 next converts the predicted strength level by the selected visual-haptic model into a physical feedback signal (step 310). In some embodiments, step 310 can be performed by the above-described haptic-feedback generation module 104 in FIG. 1B. In other embodiments, the output of the selected visual-haptic model can be fed to a UID of the robotic surgical system, which then converts the predicted strength level into the physical feedback signal. Finally, process 300 communicates the converted physical feedback signal to the surgeon performing the surgical task as a haptic cue via the UID of the robotic surgical system (step 312). Hence, the surgeon can directly "feel" the real-time strength level of the surgical tool-tissue interaction through the haptic cue without having to use the visual haptic based on what is seen in the video image. Based on the haptic cue, the surgeon can quickly adjust the force on the surgical tools to effectuate a desirable strength level on the tissue being manipulated.

In some embodiments, the set of predetermined strength levels can include a maximum-safe strength level representing a safety threshold for the tissue under the applied force, and at least one more strength level above the maximum-safe strength level. In these embodiments, if the predicted strength level at step 308 is a strength level above the maximum-safe strength level, process 300 can additionally generate a warning signal at step 310, such as an alarm, which is then communicated to the surgeon at step 312.

As described above, the physical feedback signal generated at step 310 can take one of a number of forms that can be quickly understood by the surgeon performing the surgical task. For example, the physical feedback signal can be a visual signal that can be displayed on a monitor of the UID for the surgeon to view, or an auditory feedback signal that can be played through a speaker of the UID for the surgeon to hear. If an auditory feedback signal is used to represent the predicted strength level, the system can use different volumes or pitches of the audio sound to represent different predicted strength levels to the surgeon.

The physical feedback signal can also be a mechanical feedback signal such as a vibration that can be directly felt by the surgeon. If a mechanical vibration is used, the UID of the robotic surgical system can be configured to transmit the mechanical vibration to the hands or arms of the surgeon through one or both handheld controllers of the UID. In some embodiments, the converted mechanical vibration can use the amplitude or frequency of the vibration to represent the predicted strength levels, wherein a higher amplitude or a higher frequency indicates a higher strength level, and a lower amplitude or a lower frequency indicates a lower strength level. Another form of mechanical feedback signal may be made of a series of discrete pulses, wherein the number of pulses can be used to represent the predicted strength levels. For example, when used to evaluate the tightness of surgical knots with three predetermined tightness levels, a single pulse can indicate a loose knot, two pulses can indicate a moderate tightness knot, and three pulses can indicate a tight knot.

In the above-described step 308 of process 300, in some embodiments, to facilitate the selected visual-haptic model to perform a more reliable image classification, the surgeon performing the surgical task can intentionally pause to create a short latency during the surgical task, i.e., by holding the tissue steadily for a short period of time (e.g., a few seconds). For example, the surgeon can take the pause when the surgeon decides that a right amount of force has been applied to the tissue. In some embodiments, this short latency can be recognized by the selected visual-haptic model and subsequently triggers the model to perform the intended image classification. In this manner, the selected visual-haptic model only assesses the strength levels for the video frames captured during this latency, and the outputs from the visual-haptic model during this latency would stay the same. As a result, the haptic feedback signal received by the surgeon during this latency is also a constant, which allows the surgeon more time to understand the haptic cue, and more time to react based on the haptic cue, e.g., to either increase or decrease the applied force if the haptic cue indicates that the strength level is too low or too high, or to follow through with the surgical task if the haptic cue indicates that the strength level is just right.

In some robotic surgical systems, pressure sensors may be integrated with certain surgical tools, such as staplers, to measure direct pressure applied by these surgical tools when they are applied to tissues. Hence, for certain types of surgical tool-tissue interactions, these sensors can provide some haptic feedback to the surgeon performing the corresponding surgical tasks. However, for many types of surgical tool-tissue interactions involving one or more surgical tools pulling on a tissue, these sensor data cannot be individually used or combined in a meaningful way to indicate the correct tension level applied by the one or more tools on the tissue. This is partially due to the fact that a pressure sensor is designed to measure the compression force on a tissue, but not a tensile force applied on a tissue by pulling on the tissue. When the tension on the tissue is caused by two or more tools pulling at the tissue at the same time in different directions, it becomes even more difficult to determine the overall tension level on the tissue based on the outputs of pressure sensors integrated with the two or more tools.

In contrast, the disclosed visual-haptic feedback system and technique are capable of predicting the tension levels applied on a tissue regardless of the number of surgical tools interacting with the tissue. This is because the disclosed visual-haptic feedback system and technique are based on analyzing the overall visual appearance of the surgical tool-tissue interaction. Using the machine learning technique, the disclosed visual-haptic feedback system and technique predict the correct tension levels on a tissue by recognizing patterns within the visual appearance of the surgical tool-tissue interaction, which is independent of the number of tools involved and the nature of the applied force (whether compression or tension). Consequently, the disclosed visual-haptic feedback system and technique provide a highly flexible and significantly more accurate alternative to both the sensor-based haptic feedback technique and the conventional visual haptic technique. The disclosed visual-haptic feedback system and technique can be extremely effective when they are used to classify highly complex types of surgical tool-tissue interactions.

In some embodiments, the strength level of a given type of surgical tool-tissue interaction can be determined by combining the prediction from the disclosed visual-haptic feedback technique and the measurement from a pressure sensor integrated at the tip of a surgical tool involved in the interaction. In these embodiments, the sensor measurement can be used as an additional safeguard against excessive pressure, in the event that the visual-haptic feedback technique is unable to detect such an excessive pressure. For example, if the prediction by the visual-haptic model indicates a moderate strength level, but the pressure sensor measurement indicates a pressure level exceeding a maximum threshold, a warning signal can still be generated to warn the surgeon that an excessive pressure is detected. Note also that when the target type of surgical tool-tissue interaction involves pulling on the tissue with a tensile force, the pressure sensor measurement can also be used as a safeguard against excessive pressure on the tissue applied by the one or more tools pulling on the tissue.

In some embodiments, the disclosed visual-haptic feedback system is also configured to send physical feedback signals (e.g., a mechanical vibration) when the determined strength level is either below a minimum strength threshold or above a maximum strength threshold. In some embodiments, the feedback signal is only sent to the surgeon when the determined strength level has reached the maximum threshold. Once a physical feedback signal, such as a vibration is received, it serves as a warning for the surgeon to stop applying further pressure or tension on the tissue.

Note that the application of the disclosed visual-haptic feedback system is not limited to providing real-time haptic feedback assistance. In some embodiments, the disclosed visual-haptic feedback system can be used in an offline mode to perform procedure video analysis and generate scores for skill assessments. More specifically, the disclosed visual-haptic feedback system can be used to process a recorded video containing image frames depicting a given type of surgical tool-tissue interaction. For example, a visual-haptic model can be used to determine the amount of tension applied on the tissue by a grasper when a cautery operation is being performed. Again, the model can classify the images depicting the tissue under tension during the cautery as one of the predetermined tension levels. If the determined tension level when the cautery begins is too high or too low, a low skill score could be assigned to the recorded cautery operation. If the determined tension level when the cautery begins is one of the intermediate tension levels, a high skill score could be assigned to the recorded cautery operation. Consequently, the disclosed visual-haptic feedback system can be used to provide both real-time feedback and post-procedure analysis for the surgeons operating on robotic surgical platforms.

Exemplary Types of Surgical Tool-Tissue Interactions

1. Multiple Tool Example—Suture

During a robotically assisted suture operation, a series of surgical knots are tied with two forceps, each of which is operated by one hand of the surgeon on a remote control console. Generally, an ideal surgical knot should be sufficiently tight to firmly hold together two pieces of tissues, but at the same time not overly tight to avoid causing bleeding, leaving impressions in the tissues, and/or other complications. More specifically, the tightness of the knot is increased by pulling on the knot with one or both of the two forceps. Because the surgeon cannot physically feel the tightness of the knot applied on the tissue through the forceps, the surgeon generally determines the tightness of the knot based on the visual appearance of each knot being tied on the video monitor. As a result, there can be a vast inconsistency in gauging the tightness of a given knot from one surgeon to another surgeon. Note that in the suture example typically one or two surgical tools are used to generate the tension on the knot.

Figure 4:
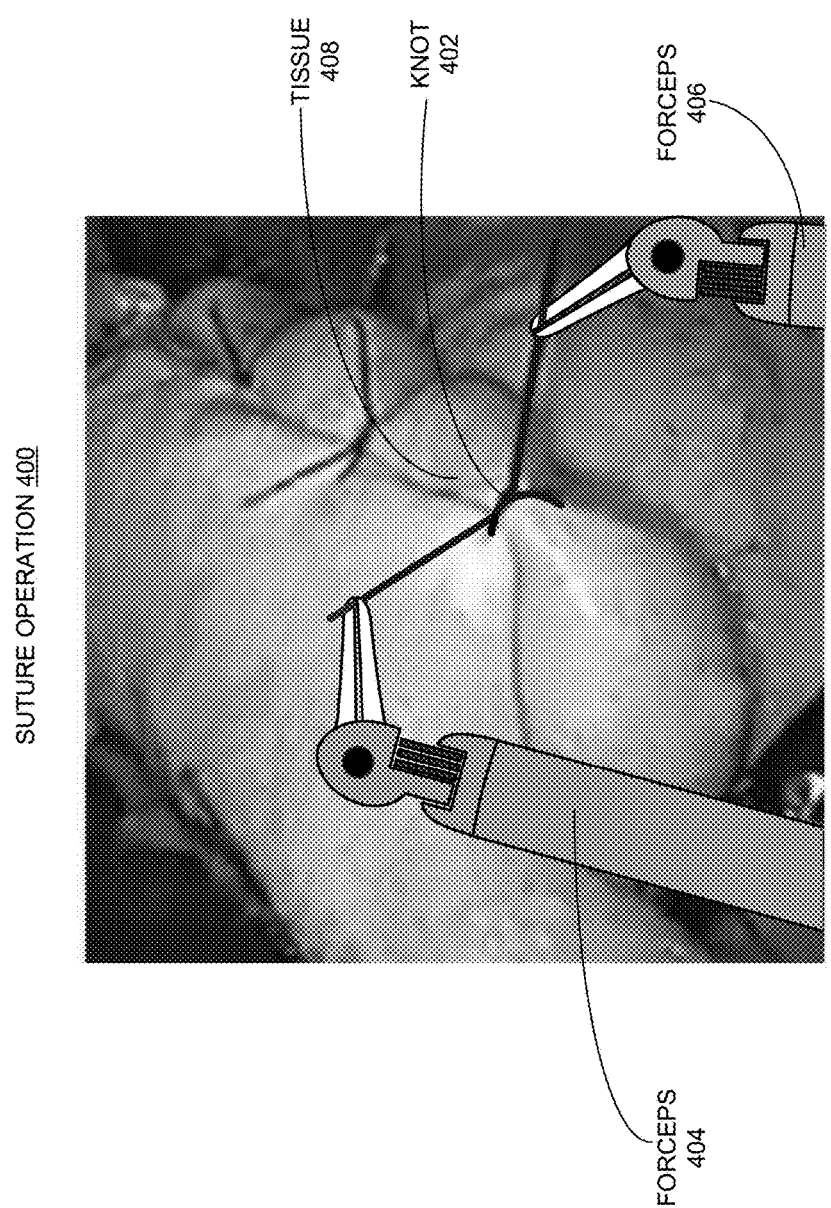
FIG. 4 shows a combined photographic and schematic image depicting a suture operation wherein a series of surgical knots are being tied in accordance with some embodiments described herein.

The disclosed visual-haptic feedback system provides a standardized machine learning-based technique to automatically classify each knot at a given time as one of a set of predetermined tightness levels, and subsequently generate a physical feedback signal based on the model classification of the knot that is then communicated to the surgeon performing the surgical task as a physical haptic feedback. FIG. 4 shows a combined photographic and schematic image depicting a suture operation 400 wherein a series of surgical knots are being tied in accordance with some embodiments described herein. As shown in FIG. 4, a knot 402 is being pulled by two surgical forceps 404 and 406 (shown as schematics superimposed over the photographic image) from both ends of knot 402 (not shown) to make a very tight knot 402. Note that the amount of deformation of the tissue 408 under the compression of knot 402 can be clearly observed, indicating a tight knot 402. As described above, a trained machine-learning model can be used to infer/predict the tightness level of knot 402 based on the shape of surgical knot 402, or the shape of tissue 408 in the vicinity of knot 402, or the combination of the two shapes.

2. Single Tool Example—Cautery

During a cautery task during a given robotic surgical procedure, a surgeon firmly holds the tissue to be cauterized with a grasper so that the tissue is under tension. In the case of cautery, a grasper operated with one hand is used to lift up a floppy tissue and place the tissue under tension to allow a cautery tool controlled with the other hand to cauterize the tissue. The applied tension causes an amount of tensile stress on the tissue to elongate the tissue in the general direction of the applied tension. In the cautery task, it is necessary to pull on the tissue with the grasper with a force that is neither too tight nor too loose. Pulling on the tissue too tightly could cause direct damage and/or injury to the tissue or an organ attached to the tissue, whereas pulling on the tissue too loosely does not create sufficient tension on the area of the tissue for the cautery tool to make a proper cut.

Figure 5:
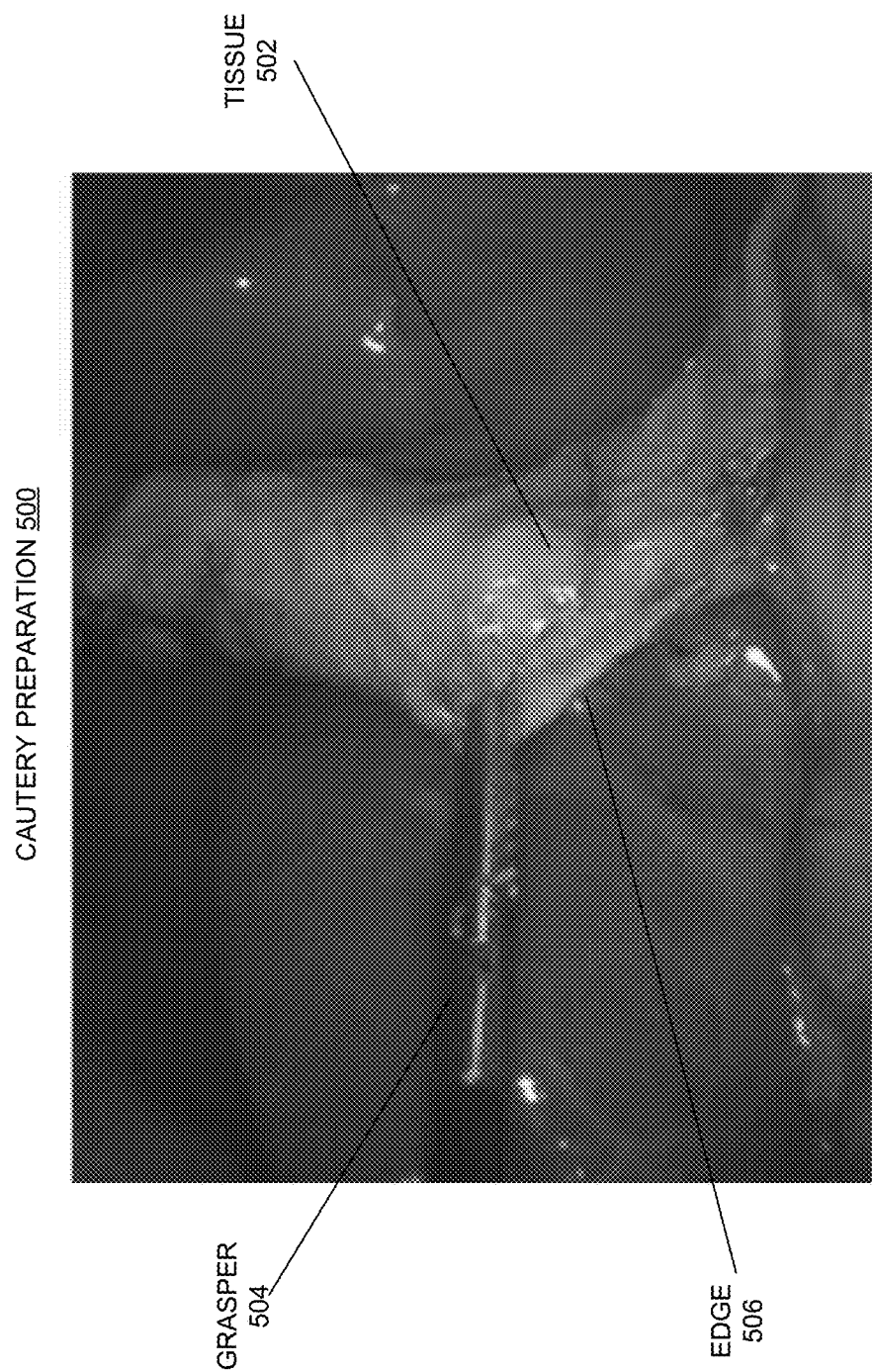
FIG. 5 shows a photographic image depicting a cautery preparation step during a robotic surgical procedure wherein a tissue to be cauterized is being pulled by a grasper in accordance with some embodiments described herein.

FIG. 5 shows a photographic image depicting a cautery preparation 500 during a robotic surgical procedure wherein a tissue 502 to be cauterized is being pulled by a grasper 504 in accordance with some embodiments described herein. As shown in FIG. 5, tissue 502 is being pulled by a single tool, i.e., grasper 504 toward the left. Note that the change of the shape of tissue 502 caused by the tension applied by grasper 504 is clearly visible in the image. Particularly, the portion of the edge 506 of tissue 502 below grasper 504 forms almost a straight line, indicating a high tension level. However, the precise amount of tension applied by grasper 504 on tissue 502 is unknown to the surgeon performing during the robotic surgical procedure because the surgeon cannot physically feel the tension applied on the tissue through the grasper. Instead, the surgeon typically determines the applied tension on the tissue based on the visual appearance of the tissue under tension, e.g., the shape of edge 506 of tissue 502. However, there can be a vast inconsistency in gauging the tension level on the tissue from one surgeon to another surgeon. Note that in the cautery example typically just one surgical tool is used to generate the required tension on the tissue.

As mentioned above, the shape of the tissue under tension indicates how tightly or loosely the grasper is pulling on the tissue and, hence, can be used to train a visual-haptic model to automatically classify an image of the tissue under tension as one of the predetermined tension levels. The disclosed visual-haptic feedback system provides a standardized machine learning-based technique to apply a constructed machine learning model to the video images depicting tissue-pulling such as cautery preparation image 500 to automatically classify the tissue-pulling depicted in the image as one of a set of predetermined tightness/tension levels, and subsequently generate a physical feedback signal based on the model classification of the tissue-pulling that is then communicated to the surgeon performing the surgical task as a physical haptic feedback.

3. Single Tool Example—Stapling

When a stapler is used in the robotic surgery to separate a tissue, the two jaws of the stapler hold the tissue from both sides of the tissue. To obtain an optimal stapling result, the jaws clamp down on the tissue between them for a certain amount of time to squeeze out fluid and air within the tissue in order to reach a certain thickness ideal for stapling. If the stapler fires prior to reaching the ideal thickness of the tissue, the staples can end up open or malformed (e.g., being partially open), thereby causing poor stapling results. However, determining exactly when to fire the stapler can be tricky. The time required to squeeze the tissue to the ideal thickness can vary greatly and, therefore, is generally not a reliable indicator. A pressure sensor integrated with the stapler can measure the pressure applied by the jaws on the tissue. However, the correlation between the pressure on the tissue and the tissue thickness is generally not consistent enough to be used to determine when the desired tissue thickness is reached. In this single tool example, the disclosed visual-haptic feedback system can be used to determine when the desired tissue thickness is reached and when the stapler should be fired.

To do so, a visual-haptic model is first trained to generate a stapler/tissue classifier. To train the model, the training data have to be collected. In some embodiments, the training data can be generated by analyzing images containing interactions of the pre-firing stapler and the tissue. The images can be annotated based on the thickness of the tissue between the jaws of the stapler, or based on the shape of the stapler, or a combination of the above. For example, the shape of the stapler can include the angle between the two jaws. When the stapler is first applied on the tissue, the angle between the two jaws is usually at the largest level. As the tissue is compressed, the jaws begin to close onto each other and the angle between the jaws decreases. At a certain point, an optimal jaw angle can be reached for firing. Moreover, as the two jaws compress the tissue, the tissue continues to deform. Hence, annotating the images for ground truth can be based on both the shape of the jaws and the shape of the tissue being compressed. In some embodiments, a set of compression intensity levels can be defined, e.g., light, medium, and high, with the high compression level corresponding to the ideal firing condition. Note that the disclosed visual-haptic feedback system and technique can replace the time-counting technique to determine a proper firing time. It can be understood that the disclosed visual-haptic feedback technique can be significantly more accurate in terms of determining when firing should occur because it is based on a direct observation of the tissue thickness, whereas the timing is an indirect indication of the tissue thickness.

Note that in the staple example, the pressure sensor data can be used in combination with the visual-haptic model to assist determining an optimal timing for firing the stapler. In one embodiment, the visual-haptic model determines if the correct thickness of the tissue has been reached based on the configuration of the tool, i.e., if the jaws are closed properly. However the firing of the stapler may not be triggered if the pressure sensor measurement indicates that a sufficient pressure has not been applied to the tissue.

Figure 6:
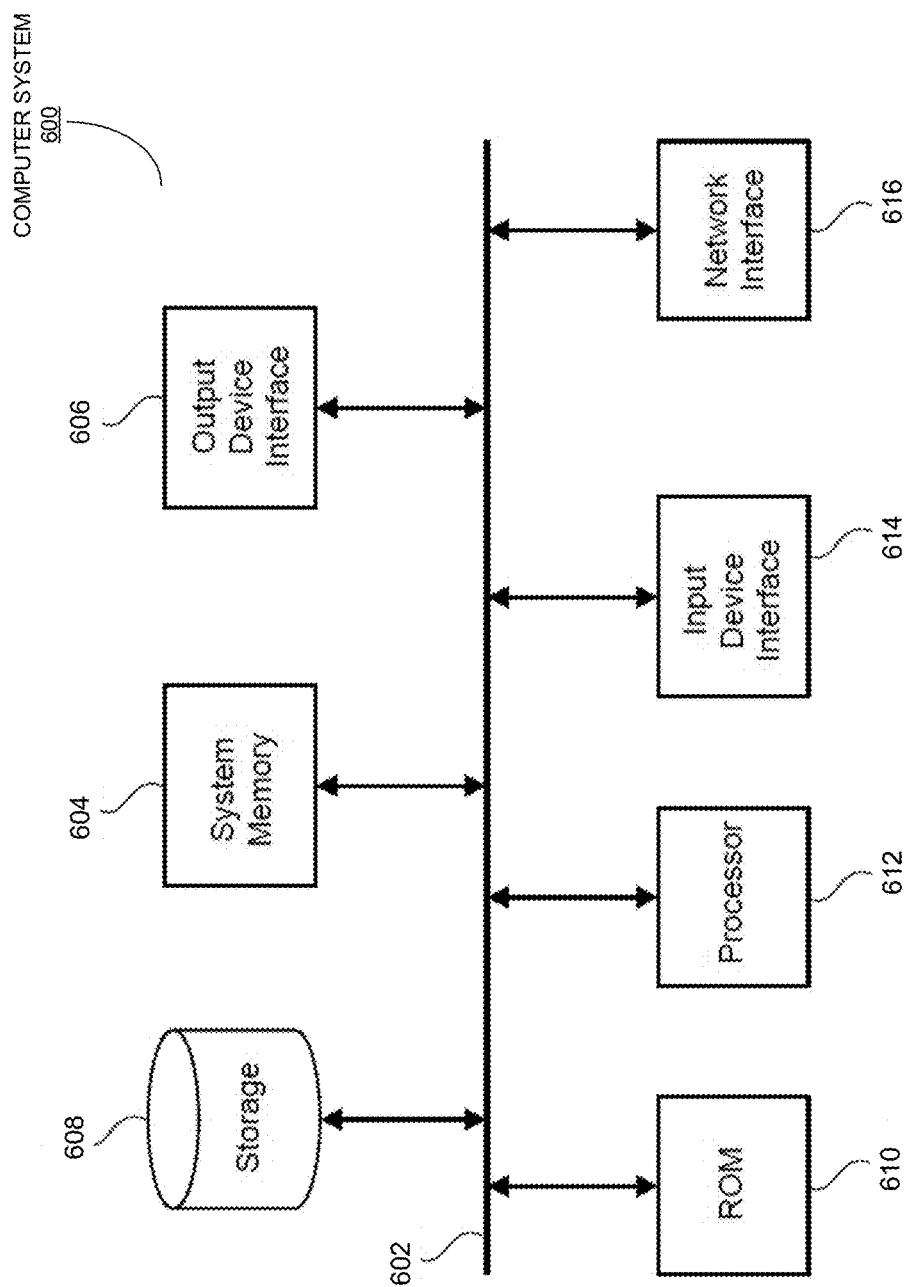
FIG. 6 conceptually illustrates a computer system with which some embodiments of the subject technology can be implemented.

FIG. 6 conceptually illustrates a computer system with which some embodiments of the subject technology can be implemented. Computer system 600 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 600 includes a bus 602, processing unit(s) 612, a system memory 604, a read-only memory (ROM) 610, a permanent storage device 608, an input device interface 614, an output device interface 606, and a network interface 616. In some embodiments, computer system 600 is a part of a robotic surgical system.

Bus 602 collectively represents all system, peripheral, and chipset buses that communicatively connect the numerous internal devices of computer system 600. For instance, bus 602 communicatively connects processing unit(s) 612 with ROM 610, system memory 604, and permanent storage device 608.

From these various memory units, processing unit(s) 612 retrieves instructions to execute and data to process in order to execute various processes described in this patent disclosure, including the above-described processes of constructing new visual-haptic models and providing a surgeon operating in a robotic surgical system with real-time haptic feedback using the trained visual-haptic models described in conjunction with FIGS. 1B and 2-3. The processing unit(s) 612 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 612 can be a single processor or a multi-core processor in different implementations.

ROM 610 stores static data and instructions that are needed by processing unit(s) 612 and other modules of the computer system. Permanent storage device 608, on the other hand, is a read-and-write memory device. This device is a non-volatile memory unit that stores instructions and data even when computer system 600 is off. Some implementations of the subject disclosure use a mass-storage device (such as a magnetic or optical disk and its corresponding disk drive) as permanent storage device 608.

Other implementations use a removable storage device (such as a floppy disk, flash drive, and its corresponding disk drive) as permanent storage device 608. Like permanent storage device 608, system memory 604 is a read-and-write memory device. However, unlike storage device 608, system memory 604 is a volatile read-and-write memory, such as a random access memory. System memory 604 stores some of the instructions and data that the processor needs at runtime. In some implementations, various processes described in this patent disclosure, including the processes of establishing machine learning targets, segmenting and mining surgical videos of different surgical procedures, and training machine learning classifiers for automatically tagging surgical videos in conjunction with FIGS. 1-5, are stored in system memory 604, permanent storage device 608, and/or ROM 610. From these various memory units, processing unit(s) 612 retrieves instructions to execute and data to process in order to execute the processes of some implementations.

Bus 602 also connects to input and output device interfaces 614 and 606. Input device interface 614 enables the user to communicate information to and select commands for the computer system. Input devices used with input device interface 614 include, for example, alphanumeric keyboards and pointing devices (also called "cursor control devices"). Output device interface 606 enables, for example, the display of images generated by the computer system 600. Output devices used with output device interface 606 include, for example, printers and display devices, such as cathode ray tubes (CRT) or liquid crystal displays (LCD). Some implementations include devices such as a touch-screen that functions as both input and output devices.

Finally, as shown in FIG. 6, bus 602 also couples computer system 600 to a network (not shown) through a network interface 616. In this manner, the computer can be a part of a network of computers (such as a local area network ("LAN"), a wide area network ("WAN"), an intranet, or a network of networks, such as the Internet. Any or all components of computer system 600 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for generating a haptic feedback based on a captured endoscopic video depicting an interaction between one or more surgical tools and a tissue during a robotic surgical procedure, the method comprising:
   receiving an endoscopic video captured for a surgical procedure performed on a robotic surgical system;
   detecting a surgical task in the endoscopic video that involves a given type of surgical tool-tissue interaction caused by applying a force on a tissue using one or more surgical tools;
   selecting a machine learning model from a set of machine learning models based on the detected surgical task, wherein each machine learning model in the set of machine learning models is trained to analyze a given type of surgical tool-tissue interaction;

for a video image or a sequence of video images associated with the detected surgical task depicting the given type of surgical tool-tissue interaction, applying the selected machine learning model to the video image or the sequence of video images to predict a strength level of the depicted surgical tool-tissue interaction; and providing the predicted strength level to a surgeon performing the surgical task as a haptic feedback signal for the given type of surgical tool-tissue interaction.

2. The computer-implemented method of claim 1, wherein detecting the surgical task in the endoscopic video involving the given type of surgical tool-tissue interaction includes detecting one or more surgical tools coming into view.

3. The computer-implemented method of claim 1, wherein the selected machine learning model is trained to classify a video image or a sequence of video images depicting the given type of surgical tool-tissue interaction as one of a set of predetermined strength levels defined for the given type of surgical tool-tissue interaction.

4. The computer-implemented method of claim 3, wherein applying the selected machine learning model to the video image or the sequence of video images to predict the strength level of the depicted surgical tool-tissue interaction includes classifying the video image or the sequence of video images as one of the set of predetermined strength levels for the given type of surgical tool-tissue interaction based on analyzing a visual appearance of the depicted surgical tool-tissue interaction.

5. The computer-implemented method of claim 3, wherein the set of predetermined strength levels includes a maximum strength level, and wherein if the predicted strength level is determined to be above the maximum strength level, the method further comprises generating a warning signal to be communicated to the surgeon.

6. The computer-implemented method of claim 1, wherein providing the predicted strength level to the surgeon performing the surgical task includes:

converting the predicted strength level by the selected machine learning model into a physical feedback signal; and communicating the converted physical feedback signal to the surgeon performing the surgical task via a user interface device (UID) of the robotic surgical system.

7. The computer-implemented method of claim 6, wherein the physical feedback signal is a mechanical vibration, and wherein communicating the converted physical feedback signal to the surgeon via the UID of the robotic surgical system includes transmitting the mechanical vibration to a remote controller of the UID held by the surgeon so that the surgeon can directly feel the physical feedback signal.

8. The computer-implemented method of claim 7, wherein the method further comprises using different frequencies or different intensities of the mechanical vibration to represent different predicted strength levels of the given type of surgical tool-tissue interaction.

9. The computer-implemented method of claim 6, wherein the physical feedback signal is an auditory signal, and wherein communicating the converted physical feedback signal to the surgeon via the UID of the robotic surgical system includes transmitting the auditory signal using a speaker of the UID so that the surgeon can directly hear the physical feedback signal.

10. The computer-implemented method of claim 9, wherein the method further comprises using different volumes or different pitches of the auditory signal to represent different predicted strength levels of the given type of surgical tool-tissue interaction.

11. The computer-implemented method of claim 1, wherein the given type of surgical tool-tissue interaction is caused by applying a compression force on the tissue using the one or more surgical tools.

12. The computer-implemented method of claim 1, wherein the given type of surgical tool-tissue interaction is caused by applying a tensile force on the tissue using the one or more surgical tools.

13. The computer-implemented method of claim 1, wherein the given type of surgical tool-tissue interaction is caused by applying the force using a single surgical tool on the tissue.

14. The computer-implemented method of claim 1, wherein the given type of surgical tool-tissue interaction is caused by applying the force using two or more surgical tools on the tissue.

15. The computer-implemented method of claim 1, wherein the given type of surgical tool-tissue interaction is associated with one of:

tying a surgical knot during a suture operation;
pulling on the tissue during a cautery operation; and
compressing the tissue during a stapling operation.

16. The computer-implemented method of claim 1, wherein prior to using the selected machine learning model, the method further comprises training the selected machine learning model by:

receiving a set of endoscopic videos;
processing each of the endoscopic videos to extract from the endoscopic video one or more segments that depict the given type of tool-tissue interaction;
for each of the extracted video segments, annotating video images depicting the given type of tool-tissue interaction according to a set of predetermined strength levels; and
using the annotated video images as ground truth information to train a machine learning model to analyze the given type of surgical tool-tissue interaction.

17. A system for generating a haptic feedback based on captured endoscopy images depicting an interaction between one or more surgical tools and a tissue during a robotic surgical procedure, the system comprising:

one or more processors;
a memory coupled to the one or more processors;
a receiving module configured to receive an endoscopic video captured for a surgical procedure performed on a robotic surgical system;
a detection module configured to detect a surgical task in the endoscopic video that involves a given type of surgical tool-tissue interaction caused by applying a force on a tissue using one or more surgical tools;
a selection module configured to select a machine learning model from a set of machine learning models based on the detected surgical task, wherein each machine learning model in the set of machine learning models is trained to analyze a given type of surgical tool-tissue interaction;
a machine learning module configured to, for a video image or a sequence of video images associated with the detected surgical task depicting the given type of surgical tool-tissue interaction, apply the selected machine learning model to the video image or the sequence of video images to predict a strength level of the depicted surgical tool-tissue interaction; and a user interface module configured to provide the predicted strength level to a surgeon performing the surgical task as a haptic feedback signal for the given type of surgical tool-tissue interaction.

18. The system of claim 17, wherein the system further comprises a machine-learning-model training module configured to train the selected machine learning model by:

receiving a set of endoscopic videos;

processing each of the endoscopic videos to extract from the endoscopic video one or more segments that depict the given type of tool-tissue interaction;

for each of the extracted video segments, annotating video images depicting the given type of tool-tissue interaction according to a set of predetermined strength levels; and using the annotated video images as ground truth information to train a machine learning model to analyze the given type of surgical tool-tissue interaction.

19. A robotic surgical system, comprising:

one or more surgical tools each coupled to a robotic arm;

an endoscope configured to capture endoscopic videos;

a receiving module configured to receive a captured endoscopic video for a surgical procedure performed on the robotic surgical system;

a detection module configured to detect a surgical task in the endoscopic video that involves a given type of surgical tool-tissue interaction caused by applying a force on a tissue using the one or more surgical tools;

a selection module configured to select a machine learning model from a set of machine learning models based on the detected surgical task, wherein each machine learning model in the set of machine learning models is trained to analyze a given type of surgical tool-tissue interaction;

a machine learning module configured to, for a video image or a sequence of video images associated with the detected surgical task depicting the given type of surgical tool-tissue interaction, apply the selected machine learning model to the video image or the sequence of video images to predict a strength level of the depicted surgical tool-tissue interaction; and a user interface module configured to provide the predicted strength level to a surgeon performing the surgical task as a haptic feedback signal for the given type of surgical tool-tissue interaction.

20. The robotic surgical system of claim 19, wherein the robotic surgical system further comprises a machine-learning-model training module configured to train the selected machine learning model by:

receiving a set of endoscopic videos;

processing each of the endoscopic videos to extract from the endoscopic video one or more segments that depict the given type of tool-tissue interaction;

for each of the extracted video segments, annotating video images depicting the given type of tool-tissue interaction according to a set of predetermined strength levels; and using the annotated video images as ground truth information to train a machine learning model to analyze the given type of surgical tool-tissue interaction.

* * * * *

UNITED STATES PATENT AND TRADEMARK OFFICE
CERTIFICATE OF CORRECTION

PATENT NO. : 10,383,694 B1
APPLICATION NO. : 16/129593
DATED : August 20, 2019
INVENTOR(S) : Jagadish Venkataraman et al.

It is certified that error appears in the above-identified patent and that said Letters Patent is hereby corrected as shown below:

On the Title Page

In Item (73), under Assignees, at Lines 1-5, delete "JOHNSON & JOHNSON INNOVATION - JJDC, INC., New Brunswick, NJ (US); VERILY LIFE SCIENCES LLC, South San Francisco, CA (US)" and insert --VERB SURGICAL INC., Mountain View, CA (US)--

Signed and Sealed this
Thirtieth Day of June, 2020

Andrei Iancu
*Director of the United States Patent and Trademark Office*